(12) United States Patent
Richter

(10) Patent No.: US 10,052,180 B1
(45) Date of Patent: Aug. 21, 2018

(54) VIRTUAL DENTAL ARTICULATOR AND SYSTEM

(71) Applicant: David D. Richter, Greeley, CO (US)

(72) Inventor: David D. Richter, Greeley, CO (US)

( * ) Notice: Subject to any disclaimer, the term of this patent is extended or adjusted under 35 U.S.C. 154(b) by 0 days.

(21) Appl. No.: 15/394,552

(22) Filed: Dec. 29, 2016

(51) Int. Cl.
*A61C 9/00* (2006.01)

(52) U.S. Cl.
CPC .................. *A61C 9/0053* (2013.01)

(58) Field of Classification Search
CPC .............................. A61C 9/0053; A61C 11/02
See application file for complete search history.

(56) References Cited

U.S. PATENT DOCUMENTS

| | | | |
|---|---|---|---|
| 4,611,288 A | 9/1986 | Duret et al. | |
| 6,152,731 A * | 11/2000 | Jordan ................... | A61C 11/00 433/69 |
| 6,334,853 B1 | 1/2002 | Kopelman et al. | |
| 6,621,491 B1 | 9/2003 | Baumrind et al. | |
| 6,648,640 B2 | 11/2003 | Rubbert et al. | |
| 6,915,178 B2 | 7/2005 | O'Brien et al. | |
| 7,916,911 B2 | 3/2011 | Kaza et al. | |
| 8,099,268 B2 | 1/2012 | Kitching et al. | |
| 8,111,909 B2 | 2/2012 | Orth et al. | |
| 8,185,224 B2 | 5/2012 | Powell et al. | |
| 8,896,592 B2 | 11/2014 | Boltunov et al. | |
| 2004/0172150 A1 | 9/2004 | Perot et al. | |
| 2007/0031774 A1 | 2/2007 | Cinader, Jr. et al. | |
| 2008/0057466 A1 * | 3/2008 | Jordan ................... | A61C 11/00 433/69 |
| 2010/0054558 A1 * | 3/2010 | Kim ..................... | G05B 19/401 382/128 |
| 2013/0204600 A1 | 8/2013 | Mehra | |
| 2013/0275107 A1 * | 10/2013 | Alpern ................ | A61C 9/0053 703/11 |
| 2016/0162631 A1 * | 6/2016 | Klein ................... | A61C 19/045 703/11 |

* cited by examiner

*Primary Examiner* — Nicholas Lucchesi
(74) *Attorney, Agent, or Firm* — Ramon L. Pizarro; Edwin H. Crabtree

(57) ABSTRACT

A system and method for creating a model of a patient's mandible and any teeth supported from the mandible and manipulating the mandible relative to anatomical features of the patient's maxilla. The system uses markers positioned on the mandible and on the maxilla to create a functional mandibular axis that approximates an axis through the condyles of the patient. The functional mandibular axis and geometric and anatomical information about the patient's upper and lower jaw are then used to create prostheses for the patient. The system is also used for making corrections to the prosthesis.

5 Claims, 4 Drawing Sheets

VIRTUAL DENTAL ARTICULATOR AND SYSTEM

BACKGROUND OF THE INVENTION (a) Field of the Invention

This invention relates to methods and devices for obtaining a three-dimensional digital representation of the teeth of a patient, and then using the system for creating the three-dimensional model to generate a model of the movement of the mandible the individual relative to the maxilla by using scans of movements of the mandible to establish a condylar axis that is then used to create a virtual, digital, articulator model of the patient's teeth.

(b) Discussion of Known Art

Mechanical dental articulators have been widely used in dentistry for over a century. As in U.S. Pat. No. 582,731 to Fourt, these early devices focused on creating a mechanical device that simulated the cooperation of the human mandible and maxilla. However, the use of these early devices led to recognition of great range in anatomical variation of patients, and of the complexity of the movement of the jaw as enabled by the temporomandibular joint (TMJ). Another example of an articulator is disclosed in U.S. Pat. No. 5,957,688 to Van Valey, incorporated herein by reference.

Broadly speaking, the TMJ encompasses the condyles of the jaw, which allow rotation about a condylar axis. Importantly, the TMJ not only enables rotation but also allows translation of the condyles of the jaw. Ligaments and muscles connect the jaw to the temporal bone and favor the resting position of the jaw and condyles. This anatomical arrangement allows the jaw to achieve pure rotation about condylar axis when the condyles are nested over their respective fossae, as well as translation from the fossae with the aid of the muscles and ligaments.

Mechanical articulators simulate the coupling of a patient's jaw by combining mechanical components that can be adjusted to simulate the jaw movement of a particular patient. Proper occlusion between the upper and lower jaws of a patient is essential to maximize comfort of the patient during mastication. Additionally, proper occlusion is essential for alleviating symptoms of patients suffering from tempormandibular joint syndrome. Because such occlusion of the upper and lower jaws is so closely related to condylar movement about the tempormandibular joint, a complete understanding of the movement of the patient's lower jaw about a hinge axis defined by the patient's condyles.

While a dominant factor of occlusal and candylar motion includes pivotal movement of the lower jaw about a hinge axis through the TMJ, other factors such as a patient's unique anatomical characteristics also affect the movement of the jaw. Accordingly, it has been quite difficult to not only record a comprehensive range of mandibular movement, but also precisely replicate this movement with precision through the use of mechanical dental articulators.

For decades, computerized systems have been adapted for modeling mandibular movements. These systems have the ability to create accurate three-dimensional models of a patient's teeth. An example of such a system is disclosed in U.S. Pat. No. 5,905,658 to Baba, and incorporated herein by reference in its entirety, and yet nother example is found in U.S. Pat. No. 7,824,346 to Marshall, incorporated herein by reference in its entirety. While computerized systems do provide advantages in their ability to manipulate large amounts of data describing the details of a patient's anatomy, it has been recognized that despite the accuracy in creating digital images of teeth, these systems still require the verification of the correctness of the resulting products through the use of an articulator, such as the Van Valey articulator mentioned above. See also, U.S. Pat. No. 8,374,714 to Dunne et al., incorporated herein by reference in its entirety, which includes a discussion of the prior art and recognition of the burdens of the unsatisfactory level in the amount of errors in prosthetics made using conventional methods. Still further, U.S. Pat. No. 6,152,731 to Jordan et al., incorporated herein by reference in its entirety, also discusses computerized methods for creating dental prostheses and for creating a virtual articulator. However, the Jordan et al. system is limited in that it relies on a model that uses vertical axial motion, instead of motion based on the actual articulation of the patient's jaw.

It can be appreciated that correction of prostheses ultimately leads to increase costs and discomfort to the patient. Accordingly, there remains a need for a system that reduces or minimizes errors in dental prosthetics.

Additionally, a review of the prior art reveals that data relating to, or describing, the actual geometry of a patient's teeth has not been used in a manner that allows the use of data collected using existing systems to be used in a manner that eliminates errors in prosthetics made with the use of this data.

A review of known devices and system reveals that there remains a need for a system that minimizes the need to use dental articulators and re-work or correct prosthesis made from data collected with digital systems.

SUMMARY

It has been discovered that problems associated with known systems can be solved by recognizing that the condyle are nested over their respective fossae when the jaw is in a closed, relaxed, position. Then, selecting one of the fossa as being a "first center fossa", and rotating the aw along a transverse plane and about the first center fossa while allowing the mating condyle to nest within the first center fossa, causes the teeth of the jaw to move along an arch on the transverse plane. Since all of the teeth of the jaw will move about a unique arc about the first center fossa, tracking of the path of the teeth as the jaw is moved allows the system to establish the location of what is defined here as a first functional condyle.

After the location first functional condyle has been established, the remaining condyle of the patient's jaw may then be rotated about the "second center fossa", along the transverse plane and the movement of the teeth used to establish the location of a second "functional condyle".

A dynamic model of the patient's teeth and bite can then be created once the first and second functional condyles have been located relative to the data defining the patient's maxillary and mandibular teeth. The first and second functional condyles are used to define the axis of rotation of the patient's jaw, and the resulting dynamic model developed providing rotation of the mandibular teeth about this "functional mandibular axis".

According to an example of the disclosed system, the data describing the maxilliary and mandibular teeth is obtained from scanning devices, such as the iTero Element® intraoral scanner available from Align Technology, Inc. of San Jose, Calif.

Accordingly, the disclosed method integrates the spatial relationship of all of the patient's teeth, including detailed information as to the actual shape of each of the teeth. The coupling of this information with the location of the functional condyles and the functional condylar axis 36 results in a system that allows the dental professionals to visualize interference during the patient's bite. Additionally, the system will allow the dental professional to occlusion plane angles in three-dimensional space, allowing the dental professional to evaluate whether the patient's teeth are positioned along the mandibles so as to provide proper occlusion of the teeth while masticating.

It is submitted that the need for mechanical articulators can be minimized by providing a digital, computerized, system that integrates the unique aspects of the condylar arrangement of a particular patients' anatomy into the digital, computerized model of a patient's teeth. Still further, there remains a need for a system that not only provides an accurate three-dimensional model of a patient's teeth, but also integrates the patient's condylar features, and thus allows modeling that integrates the patient's condylar axis and associated mandible movement to the digital model of the patient's teeth.

It should also be understood that while the above and other advantages and results of the present invention will become apparent to those skilled in the art from the following detailed description and accompanying drawings, showing the contemplated novel methods and construction, combinations of steps and elements as herein described, and more particularly defined by the appended claims, it should be clearly understood that changes in the precise embodiments of the herein disclosed invention are meant to be included within the scope of the claims, except insofar as they may be precluded by the prior art.

DRAWINGS

The accompanying drawings illustrate preferred embodiments of the present invention according to the best mode presently devised for making and using the instant invention, and in which.

DETAILED DESCRIPTION OF PREFERRED EXEMPLAR EMBODIMENTS

While the invention will be described and disclosed here in connection with certain preferred embodiments, the description is not intended to limit the invention to the specific embodiments shown and described here, but rather the invention is intended to cover all alternative embodiments and modifications that fall within the spirit and scope of the invention as defined by the claims included herein as well as any equivalents of the disclosed and claimed invention.

Figure 1:
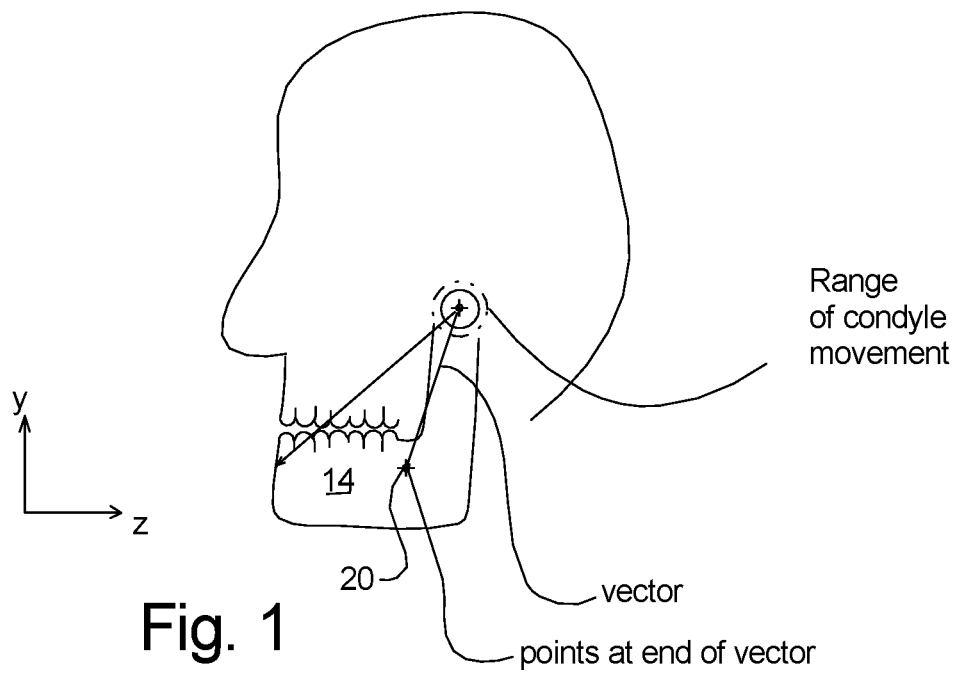
FIG. 1 illustrates the steps carried with a preferred example of the disclosed system.
Figure 2:
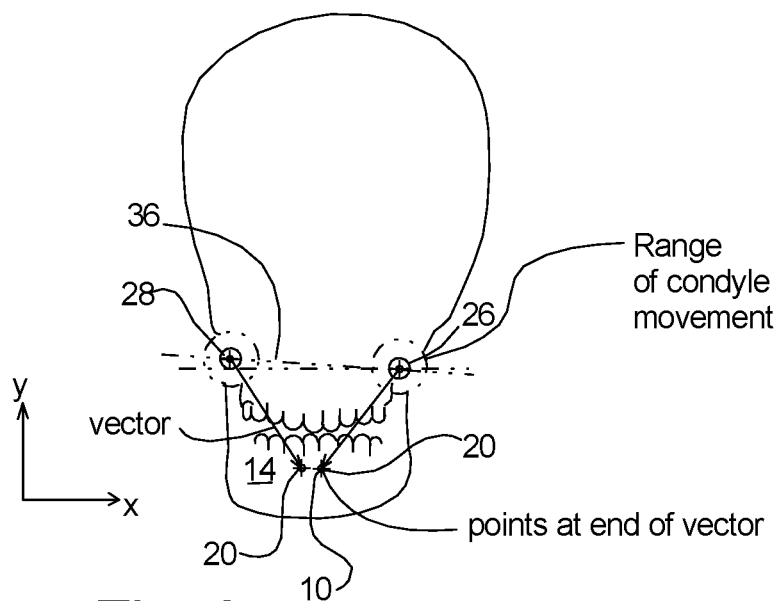
FIG. 2 illustrates movement of the condyles from the fossa.
Figure 3:
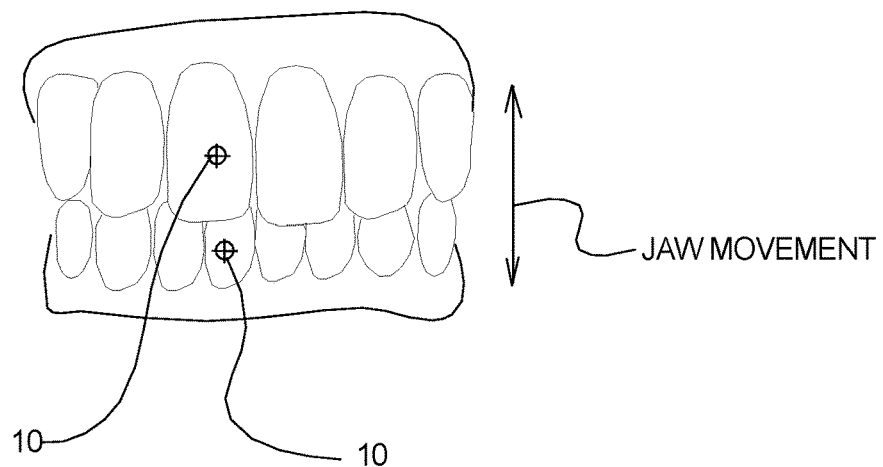
FIG. 3 illustrates the centric relation position of the patient's teeth, and movement markers placed on the patient's mating front teeth. The markers allowing the system to track the movements of the jaw relative to the stationary marker on the upper mandibule.
Figure 4:
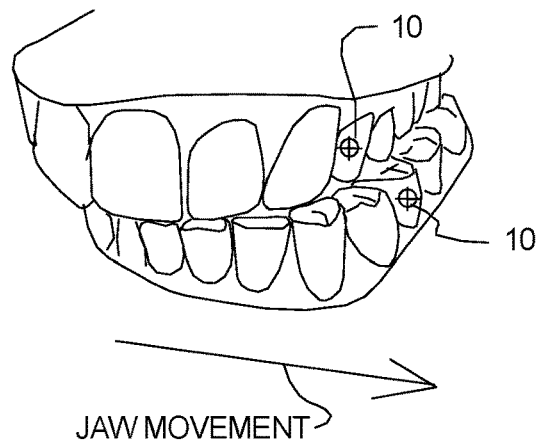
FIG. 4 illustrates the use of movement markers that are placed on a pair of mating left teeth to allow changes in distance between the teeth.
Figure 5:
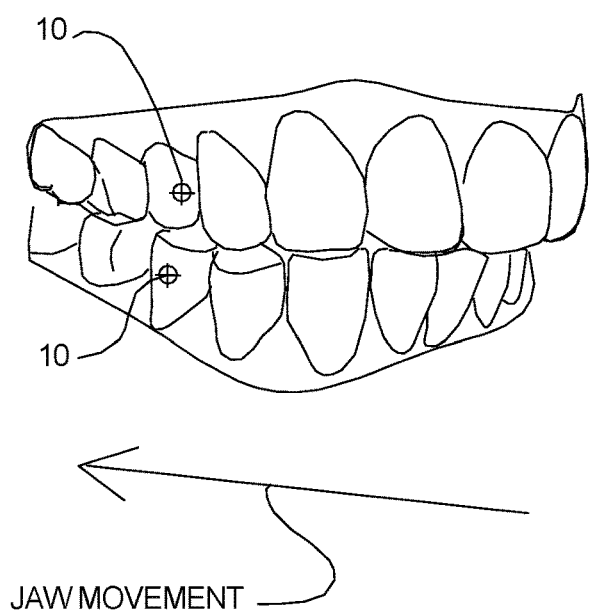
FIG. 5 illustrates the use of movement markers that are placed on a pair of mating right teeth to allow changes in distance between the teeth.

Turning now to FIG. 1 where a flow diagram of steps of the method disclosed here have been illustrated. The process begins with creating a three-dimensional digital mapping image or scan of the patient's teeth. As discussed above, it is contemplated that these three-dimensional mapping images may be created with a commercially-available dental scanner, such as the iTero Element®, and then selecting and placing or attaching at least one reference point marker 10 on a tooth 12 or on the patient's mandible 14. The reference point may be defined by placing a temporary mark on the tooth, or by temporarily attaching the marker 10 to the tooth. The marker may also be create on the patient with an innocuous ink, such as a phosphoric ink that can be revealed to a UV light detecting device. The mark or marker 10 will be used to track movement of the mandible, and thus will preferably be attached to fixed features on the mandible, such as teeth. It is preferred that the marker will be of a nature that will cause the marker 10 to appear in the scan of the patent's teeth. It is also contemplated that small markings of a contrasting color may be used, or a temporarily attached protruding and/or colored marker may also be used.

It is also contemplated that markers may also be placed on one or more of the maxillary teeth. The advantage of the use of one or more additional marker on one or more of the maxillary teeth is that the mandible moves relative to the maxilla. Tracking movements relative to a point on the maxilla or at a fixed location relative to the maxilla, such as on a maxillary tooth, will allow the use of the disclosed system to account for vertical movements of the mandible relative to the maxilla. The accounting for vertical movement of the mandible will allow the disclosed system to focus on movements of the mandible along a transverse plane, which will then allow the system to track lateral movement of the mandible.

It is also contemplated that the use of the markers will also allow the disclosed system to account for lateral, or "shifting" movements of the condyle beyond the resting position of a condyle from its respective fossa. The accounting, which in this case is the subtraction of distance traveled due to movements away from the resting position of the condyle from its respective fossa, which will be the respective lateral movement of the marker on the tooth on the mandible relative to the marker on the tooth on the maxilla. The respective lateral movement is used in the accounting to ensure that the lateral movement being accounted for is the movement due to rotation of the jaw about the relevant fossae, and not due translation of the condyles from the fossa.

Once the distance of lateral movement of the mandible has been accounted for, then the center of rotation of the marking on the tooth on the mandible can be determined. The center of rotation of movement of the mandible towards the left side will be the left functional condyle 26 location, and the center of rotation of movement of the mandible towards the right side will be the right functional condyle 28 location.

Having determined the locations of the left functional condyle and the right functional condyle, the functional condylar axis 36 is used with disclosed system will be established. This axis will then be used to simulate the movement of the patient's mandible and the mating of the patient's teeth using three dimensional representations of the surfaces of the patient's teeth.

Since the condyles are not fixedly or rigidly attached to their respective fossae, but are biased into the respective fossae by the various muscles and fibrous tissue between the mandible and the maxillary structure, it is recognized that movement of the jaw relative to the maxilla will result in rotation and translation, due to the fact that the movements are not about rigid features. However, the translation along a horizontal plane adds information as to the location of the respective functional condyles.

Figure 6:
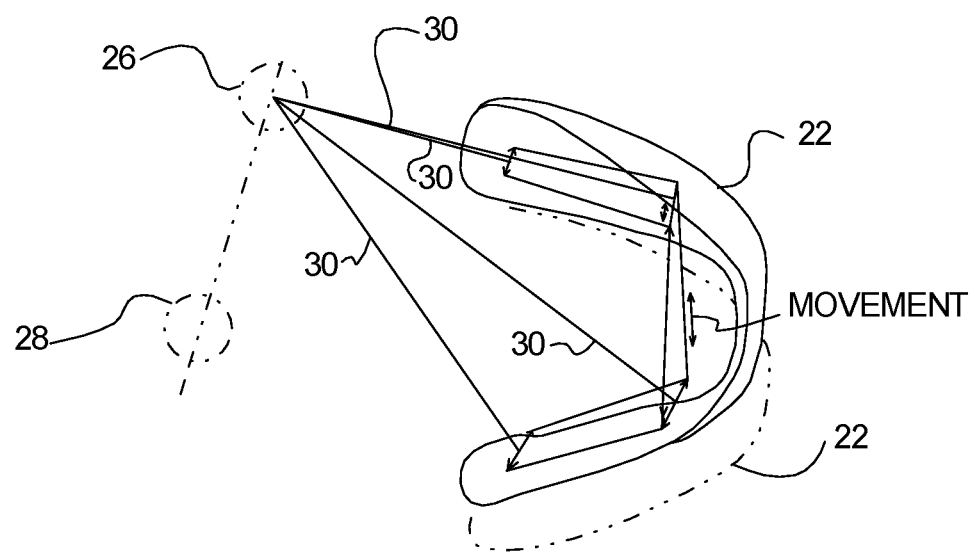
FIG. 6 illustrates the movement and geometric relationships of the patient's anatomy that are used to define the patient's left functional condyle. The right functional condyle is also shown in this figure, as well as the condylar axis as defined here.

A Mathematical Model A mathematical model associated with the disclosed system may be created and described in conjunction with FIG. 6. First a three-dimensional scans of the upper and lower arches 22 are obtained with the mandible in various positions relative to the maxillary arch 24. Examples of these positions include centric relation open and closed, left excursion, and right excursion. The surfaces of the patient's teeth in these positions are recorded in such a way that they each independently represent states where one or both of the condyles are seated completely. This is stated in an effort to emphasis that the mathematical model that is described here is based on an idealized scenario where one or both of the condyles can be instantaneously or continuously represented by centers or near perfect centers of rotation for each scanned jaw position in question. This idealized model enables the location of the condyles to be located with the following systematic applications that idealize the instantaneous or continuous transition from one position to another to be that of a rotation about a fixed point that is described in either a three dimensional or isolated two dimensional extrapolative concentric circle analysis.

The analysis begins by taking two positions where both condyles are completely seated. These positions are those in centric relation. The model will consider these two positions to share the same arbitrary yet convenient three dimensional coordinate system that will remain consistent between these two and all following scanned positions by being held constant relative to the top jaw. Preferably, a minimum of four points 20 are selected and held at the same location by markers 10 positioned on the lower jaw between these two positions and all following positions. These points or markers 10 are preferably located on the teeth of the lower jaw and positioned in such a way that two of the points a near the front of the lower arc and the other two points are located near the back of the lower arch. These points are to be identified separately in each position in such a way that they can be considered relative to each other from one position to the next. It should be noted that the unique points are only limited by a minimum of four in count.

To increase accuracy, the number of relative points on the lower arch can be increased infinitely as to be integrated over the entire scan of the lower arch. Considering each independent pair of points that are on the same relative position on the lower arch between the two positions in centric relation, a mathematical vector 30 that is either defined in three dimensions or in a two dimensional plane that is defined by related points between the two position in question. With each of these vectors defined relative to the coordinate system that is fixed relative to the upper arch, a center point on each vector can be defined and used as the tail of another set of vectors that are normal to the original vectors defined by the collection of points. This is achieved by general mathematical calculations that are particular to vector analysis. This includes but is not limited to finite vector calculations, numerical methods, and generally excepted error analysis calculations. This new set of vectors is to be referred to as the normal vector collection. The normal vector collection is collectively pointing in the direction where the vectors will collectively converge or nearly converge along an axis that ideally runs normal to the normal vector collection. This axis to be solved for via an average of the locations where the normal vector collection converge or nearly converge according to general calculus derived minimization of collected values from convergence. This final axis is to be referred to as the condyle axis and should ideally represent and axis that runs through both condyles. This is also considered the axis of rotation for instantaneous or continues motion between positions between that are considered to be in centric relation.

Similarly, the positions that have one condyle that is no longer seated (the left and right lateral excursions) are to be used to further locate the condyles. This is achieved by considering one position in centric relation where both condyles are considered seated and by considering a second position as a lateral excursion where only one condyle is considered seated. These positions are held to the same coordinate system as the previous processes here within described before. A minimum of four points are selected and held consistent on the lower jaw between these two positions and all following positions. These points are to be located on the teeth of the lower jaw and positioned in such a way that two of the points a near the front of the lower arc and the other two points are located near the back of the lower arch. These points are to be identified separately in each position in such a way that they can be considered relative to each other from one position to the next. It should be noted that the unique points are only limited by a minimum of four in count. To increase accuracy, the number of relative points on the lower arch can be increased infinitely as to be integrated over the entire scan of the lower arch. Considering each independent pair of points that are on the same relative position on the lower arch between the two positions in question, a mathematical vector that is either defined in three dimensions or as a collection of lines that are transposed into the planes of the three dimensional coordinate system that is fixed relative to the upper arch. With each of these vectors defined relative to the coordinate system that is fixed relative to the upper arch, a center point on each vector can be defined and used as the tail of another set of vectors that are normal to the original vectors defined by the collection of points. This is achieved by general mathematical calculations that are particular to vector analysis. This includes but is not limited to finite vector calculations, numerical methods, and generally excepted error analysis calculations. Similar to the first process, this new set of vectors is to be referred to as the first prime normal vector collection. The general direction of the first prime vector collection is defined by the direction in which the collection converges or most nearly converges on one point. Graphically, these vectors will converge on a point that is in line with the condyle axis. Classical differential algorithms that minimize the nearest distance between the vectors in the first prime vector collection along with solutions that lead to finite solutions will be utilized to find the optimum statistically accurate instantaneous or continuous center of rotation. Mathematically, the points defined on the lower arch are modeled as having moved from centric relation to the lateral excursion by shearing or nearly sharing a center of rotation and the path of travel sweeps a curve for which the points would create concentric circles. The focus of these curves is what is described to be found above. This focus is considered to be the location of the condyle that is considered seated in the excursion in question. If more than one excursion scan is provided for a particular condyle, the collection of positions can be used to define an approximate set of curves swept by the defined points. Any and all mathematical methods for locating the center of rotation can be utilized in locating the condyle. The information collected at this point is enough to fully define the location of one condyle. The location of the second condyle will be located with the same process executed with the lateral exertion scan or scans that consider the second condyle to be seated. The normal vector bundle defined for locating the second condyle is to be referred to as the second prime normal vector collection.

To further define the motion of the lower jaw, the instantaneous or continuous slope of the eminence is to be defined from the existing information. This is achieved by considering one position in centric relation where both condyles are considered seated and by considering a second position as a lateral excursion where only one condyle is considered seated. These positions are held to the same coordinate system discussed above.

More specifically, a number points are selected and held consistent on the lower jaw between these two positions and all following positions. These points are to be identified separately in each position in such a way that they can be considered relative to each other from one position to the next. To increase accuracy, the number of relative points on the lower arch can be increased infinitely as to be integrated over the entire scan of the lower arch. For convenience, these points may be the same as those defined in the previous processes that considered the same scans. Considering each independent pair of points that are on the same relative position on the lower arch between the two positions in question, two vectors can be defined pointing from the seated condyle location that was solved for before and each of the points in the pair. For each pair of vectors that stem from the seated condyle location, an angle can be defined between the vectors in either spherical coordinates that utilize two angles relative to the original coordinate system or by breaking the angle into the three components existing in each of the three planes that are defined by the original coordinate system. Of all these angles that are defined by the entire collection of vector pairings between these two positions, the angles should be nearly the same. If this is significantly different, proper correction can be achieved by adjusting or neglecting the angle components that are isolated to the plane that is normal to the condyle axis.

The resulting statistical angle that results from this process is then to be applied to a vector value that starts at the seated condyle and points along the condyle axis just to the point of the second condyle's seated location. This angle or collection of angle components is to be referred to as the translation angle. This vector is to maintain its magnitude but be transformed by rotating about condyle that is considered seated by the translation angle. The resulting vector defines a point that is to be considered the unseated condyle's position. For the unseated condyle in question, an eminence vector can be defined by the difference of the point at this unseated position and the already determined seated location. These values are measured relative to the original coordinate system that is held constant to the upper arch. The direction of the eminence vector describes the instantaneous or continuous translation of the condyle as it is outside of its seated location. The eminence vector for the second condyle will be located with the same process executed with the lateral exertion scan or scans that consider the second condyle to be seated.

With the seated locations of both condyles defined along with the eminence directions for each respective condyle, the motion of the virtual articulator can be achieved by allowing near ball and socket movement about each condyle point that will be aloud to translate along the direction of their respective directions of eminence.

Figure 7:
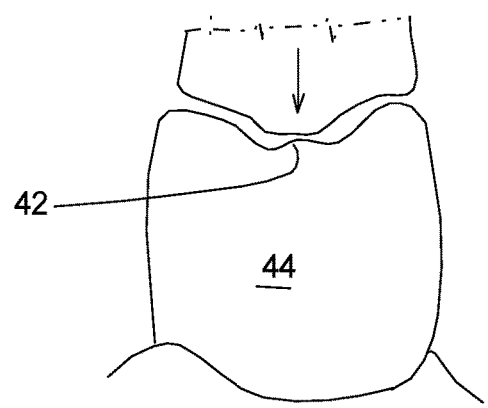
FIG. 7 illustrates a possible flaw in a prosthetic tooth.
Figure 8:
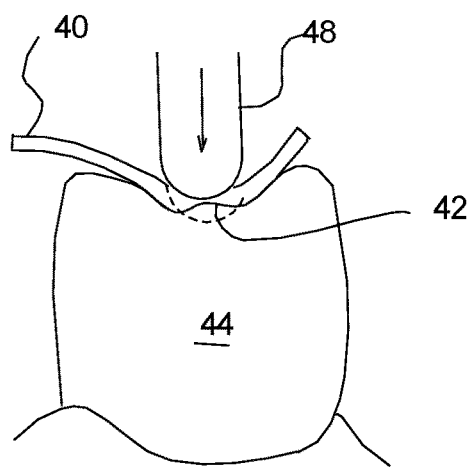
FIG. 8 illustrates the use of a gageing strip that includes a guide marker, illustrated in FIG. 9, which is used to indicate when the dentist's drill bit has removed the flaw.
Figure 9:
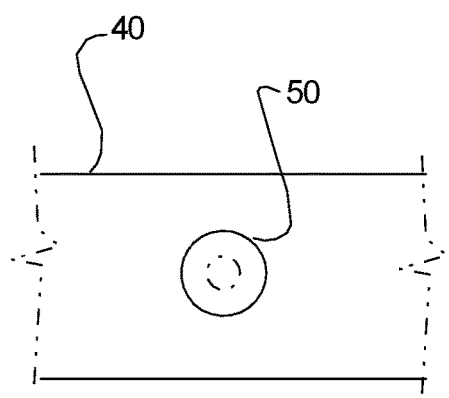
FIG. 9 Is a plan vie of a gageing strip as disclosed.

FIGS. 7-9 show a gageing strip 40 that is used to correct a flaw 42 in a prosthesis 44. The gageing strip 40 will be of a thickness that corresponds with the radius 46 or similar dimension of a drill bit 48. The gagueing strip 40 will have a marking or aperture 50 that correspond with the maximum intrusion of the drill bit 48 into the gagueing strip to indicate when the drill has removed most if not all of the flaw 42. In use, the marking or aperture 50 of the gageing strip 40 is then placed over the flaw 42, and the drill is used against the flaw 42 until the marking or aperture is filed by the drill bit 48. At this stage, most if not all of the flaw 42 will have been removed, without unnecessarily removing material from the prosthesis.

Thus it can be appreciated that the above-described embodiments are illustrative of just a few of the numerous variations of arrangements of the disclosed elements used to carry out the disclosed invention. Moreover, while the invention has been particularly shown, described and illustrated in detail with reference to preferred embodiments and modifications thereof, it should be understood that the foregoing and other modifications are exemplary only, and that equivalent changes in form and detail may be made without departing from the true spirit and scope of the invention as claimed, except as precluded by the prior art.

What is claimed is:

1. A method for creating a three-dimensional dental model of a patient having a head with teeth, including a lower jaw having mandibular teeth, the patient's teeth also comprising maxillary teeth that oppose the mandibular teeth, the maxillary teeth including maxillary tooth surfaces for use in mastication, and the mandibular teeth including mandibular tooth surfaces for use in mastication, the mandibular tooth surfaces for use in mastication mating with the maxillary tooth surfaces for use in mastication, the method comprising:

obtaining a three-dimensional map of the surfaces of the patient's maxilliary teeth;

selecting a point on a surface of a maxilliary tooth;

obtaining a three-dimensional map of the surfaces of the patient's mandibular teeth;

selecting a point on a surface of a mandibular tooth;

recording the spatial relationship between the selected point on a surface of a maxilliary tooth and the selected point on a surface of a mandibular tooth when the mandibular tooth surfaces for use in mastication are in mating contact with the maxillary tooth surfaces for use in mastication;

defining a first functional condyle location by rotating and translating the lower jaw about the head in a first direction along a transverse plane, and determining the approximate center of rotation of the lower jaw about the head, so that the first functional condyle coincides with the approximate center of rotation of the lower jaw about the head;

defining a second functional condyle location by rotating the lower jaw about the head in a second direction along the transverse plane, and determining the approximate center of rotation of the lower jaw about the head, so that the second functional condyle coincides with the approximate center of rotation of the lower jaw about the head in the second direction; and defining a functional condylar axis between the first functional condyle and the second functional condyle, so that positioning the three-dimensional map of the surfaces of the patient's maxilliary teeth with reference to the selected point on a surface of a maxilliary tooth and the selected point on a surface of a mandibular tooth allows articulation of the three-dimensional map of the surfaces of the patient's mandibular teeth of the lower jaw about the functional condilar axis.

2. A method for creating a three-dimensional dental model of a patient having a head with teeth, the teeth being on a lower jaw having mandibular teeth, the patient's teeth also comprising maxillary teeth that oppose the mandibular teeth, the maxillary teeth including maxillary tooth surfaces for use in mastication, and the mandibular teeth including mandibular tooth surfaces for use in mastication, the mandibular tooth surfaces for use in mastication mating with the maxillary tooth surfaces for use in mastication, the method comprising:

obtaining a three-dimensional map of the surfaces of the patient's maxilliary teeth;

attaching a marker at a point on a surface of a maxilliary tooth;

obtaining a three-dimensional map of the surfaces of the patient's mandibular teeth;

attaching a marker point on a surface of a mandibular tooth;

recording the spatial relationship between the selected point as defined by a marker on a surface of a maxilliary tooth and the selected point defined by a marker on a surface of a mandibular tooth when the mandibular tooth surfaces for use in mastication are in mating contact with the maxillary tooth surfaces;

defining a first functional condyle location by rotating the lower jaw about the head in a first direction along a transverse plane, and determining the approximate center of rotation of the lower jaw about the head, so that the first functional condyle coincides with the approximate center of rotation of the lower jaw about the head;

defining a second functional condyle location by rotating and translating the lower jaw about the head in a second direction along the transverse plane, and determining the approximate center of rotation and translation of the lower jaw about the head, so that the second functional condyle coincides with the approximate center of rotation and translation of the lower jaw about the head in the second direction; and defining a functional condylar axis between the first functional condyle and the second functional condyle, so that positioning the three-dimensional map of the surfaces of the patient's maxilliary teeth with reference to the selected point on a surface of a maxilliary tooth and the selected point on a surface of a mandibular tooth allows articulation of the three-dimensional map of the surfaces of the patient's mandibular teeth of the lower jaw about the functional condylar axis.

3. A method for creating a three-dimensional dental model of teeth of a patient having a head with a lower jaw, the jaw having a mental protuberance, the method comprising:

obtaining a three-dimensional map of the surfaces of the patient's jaw;

marking a point on a surface at a location near the mental protuberance;

obtaining a three-dimensional map of the surfaces of the patient's mandibular teeth;

selecting point on a surface of a mandibular tooth;

recording the spatial relationship between the selected point on a surface of a maxilliary tooth and the selected point on a surface of a mandibular tooth when the surface of the mandibular tooth surface is in mating contact with the maxillary tooth surfaces for use in mastication;

defining a first functional condyle location by rotating and translating the lower jaw about the head in a first direction along a transverse plane, and determining the approximate center of rotation of the lower jaw about the head, so that the first functional condyle coincides with the approximate center of rotation of the lower jaw about the head;

defining a second functional condyle location by rotating and translating the lower jaw about the head in a second direction along the transverse plane, and determining the approximate center of rotation of the jaw about the head, so that the second functional condyle coincides with the approximate center of rotation of the jaw about the head in the second direction; and defining a functional condylar axis between the first functional condyle and the second functional condyle, so that positioning the three-dimensional map of the maxilliary tooth surfaces of the patient with reference to the selected point on a surface of a maxilliary tooth and the selected point on a surface of a mandibular tooth allows articulation of the three-dimensional map of the surfaces of the patient's jaw.

4. A method according to claim 3 and further comprising detecting a flaw the surface of a lower mandibular tooth, the flaw comprising a protrusion along the surface of the lower mandibular tooth, and then providing a gageing strip, the gageing strip being of a thickness and having a marking that corresponds with the maximum intrusion of a drill bit into the gagueing strip such that the drilling out of the marking with the drill bit corresponds with the removal of the flaw.

5. A method according to claim 4 and further comprising detecting a flaw the surface of at least one maxilliary tooth, the flaw comprising a protrusion along the surface of the maxilliary tooth, and then providing a gageing strip, the gageing strip being of a thickness and having a marking that corresponds with the maximum intrusion of a drill bit into the gagueing strip such that the drilling out of the marking with the drill bit corresponds with the removal of the flaw.

* * * * *

UNITED STATES PATENT AND TRADEMARK OFFICE
CERTIFICATE OF CORRECTION

PATENT NO. : 10,052,180 B1
APPLICATION NO. : 15/394552
DATED : August 21, 2018
INVENTOR(S) : David D. Richter Page 1 of 2

It is certified that error appears in the above-identified patent and that said Letters Patent is hereby corrected as shown below:

In the Claims

In Column 8, Line 43 (Claim 1, Line 12) "maxilliary teeth" should read --maxillary teeth--.

In Column 8, Line 44 (Claim 1, Line 13) "a maxilliary tooth" should read --a maxillary tooth--.

In Column 8, Line 49 (Claim 1, Line 18) "a maxilliary tooth" should read --a maxillary tooth--.

In Column 9, Line 4 (Claim 1, Line 30) "maxilliary teeth" should read --maxillary teeth--.

In Column 9, Line 5 (Claim 1, Line 31) "a maxilliary tooth" should read --a maxillary tooth--.

In Column 9, Line 9 (Claim 1, Line 35) "condilar axis" should read --condylar axis--.

In Column 9, Line 21 (Claim 2, Line 12) "maxilliary teeth" should read --maxillary teeth--.

In Column 9, Lines 22-23 (Claim 2, Lines 13-14) "a maxilliary tooth" should read
--a maxillary tooth--.

In Column 9, Lines 29-30 (Claim 2, Lines 20-21) "a maxilliary tooth" should read --a maxillary tooth--.

In Column 9, Line 51 (Claim 2, Line 42) "maxilliary teeth" should read --maxillary teeth--.

In Column 9, Line 52 (Claim 2, Line 43) "a maxilliary tooth" should read --a maxillary tooth--.

In Column 10, Line 12 (Claim 3, Line 12) "a maxilliary tooth" should read --a maxillary tooth--.

In Column 10, Line 34 (Claim 3, Line 34) "a maxilliary tooth" should read --a maxillary tooth--.

Signed and Sealed this
Third Day of September, 2019

Andrei Iancu
*Director of the United States Patent and Trademark Office*

CERTIFICATE OF CORRECTION (continued)
U.S. Pat. No. 10,052,180 B1

In Column 10, Line 35 (Claim 3, Line 35) "a maxilliary tooth" should read --a maxillary tooth--.

In Column 10, Line 42 (Claim 4, Line 4) "a gageing strip" should read --a gauging strip--.

In Column 10, Line 43 (Claim 4, Line 5) "a gageing strip" should read --a gauging strip--.

In Column 10, Line 45 (Claim 4, Line 7) "a gagueing strip" should read --a gauging strip--.

In Column 10, Line 48 (Claim 5, Line 2) "one maxilliary tooth" should read --one maxillary tooth--.

In Column 10, Lines 49-50 (Claim 5, Lines 3-4) "the maxilliary tooth" should read --the maxillary tooth--.

In Column 10, Line 50 (Claim 5, Line 4) "the maxilliary tooth" should read --the maxillary tooth--.

In Column 10, Lines 50-51 (Claim 5, Lines 4-5) "the gageing strip" should read --the gauging strip--.

In Column 10, Line 54 (Claim 5, Line 7) "the gagueing strip" should read --the gauging strip--.